United States Patent [19]

Indech

[11] 4,446,229

[45] May 1, 1984

[54] METHOD OF TISSUE GROWTH

[76] Inventor: Robert B. Indech, 55 Pilgrim Rd., Melrose, Mass. 02176

[21] Appl. No.: 434,961

[22] Filed: Dec. 30, 1982

[51] Int. Cl.³ .......................... A01N 1/02; C12M 3/00
[52] U.S. Cl. ......................................... 435/1; 435/284
[58] Field of Search .................... 435/1, 240, 283, 284

[56] References Cited

U.S. PATENT DOCUMENTS

| | | | |
|---|---|---|---|
| 2,996,429 | 8/1961 | Toulmin | 435/240 |
| 3,419,473 | 12/1968 | Dawson | 435/240 |
| 3,545,221 | 12/1970 | Swenson et al. | 435/1 |
| 3,632,473 | 1/1972 | Belzer et al. | 435/1 |
| 3,883,393 | 5/1975 | Knazek et al. | 435/240 |
| 4,241,187 | 12/1980 | White | 435/284 |
| 4,339,537 | 7/1982 | Sogi et al. | 435/240 |

*Primary Examiner*—Sam Rosen

[57] ABSTRACT

An in-vitro system capable of supporting tissue growth with a blood supply is described, including a temperature and humidity controlled antiseptic chamber housing a mechanical oxygenator and waste gas removal system, a pumped continuous circulating fluid in a pipe connected to a tissue nidus, exchange membrane and circulating dialysate for waste removal, a nutrient infusion system, and a means of sterilization and immunosuppression. A total artificial life support system is described.

7 Claims, 3 Drawing Figures

METHOD OF TISSUE GROWTH

FIELD OF SEARCH

Class 435—Subclass 283.
Class 435—Subclass 284.

BACKGROUND OF THE INVENTION

Tissue growth on a nutritive surface typically reaches a critical size where continued growth necessitates a blood supply for internal nutrient delivery and waste removal. In the absence of blood supply, the critical tissue size is approximately one cubic millimeter. Cancerous tissue routinely emit angiogenesis factors to encourage capillary ingrowth. No current method exists, in vitro, to completely support tissue with a vasculature over a long period of time.

Tissue grafted from one individual to another temporarily grows and functions if a high degree of immunocompatability is present and immunosuppressive agents are employed in the host. However, the best substitute for diseased and damaged tissue is an individual is similiar healthy tissue from that same individual. In cases where conditions for growth of certain tissues in that individual are not present, a tissue substitute must be found. Although artificial organs have made considerable developmental progress, serious problems of power supply, compactability, and biological interfacing remain. In certain cases, such as severe muscular dystrophy or leukemia, no substitute is found and the individual dies. A critical need exists whereby a remaining portion of healthy tissue may be operatively removed from an individual, grown to a larger size, and then operatively substituted back within the individual to replace similiar damaged tissue.

This invention addresses these needs.

DESCRIPTION OF THE INVENTION

It is an object of the present invention to teach a method and a means by growing tissue outside of the body to a size in which its vasculature develops and is utilized for nutrient supply and waste removal.

It is an object of the present invention to teach a method and a means of growing tissue outside of the body by connecting tissue's existing vasculature to a tissue growth support system.

It is an object of the present invention to provide a method and a means for the growth of fetuses at any developmental stage.

Figure 1:
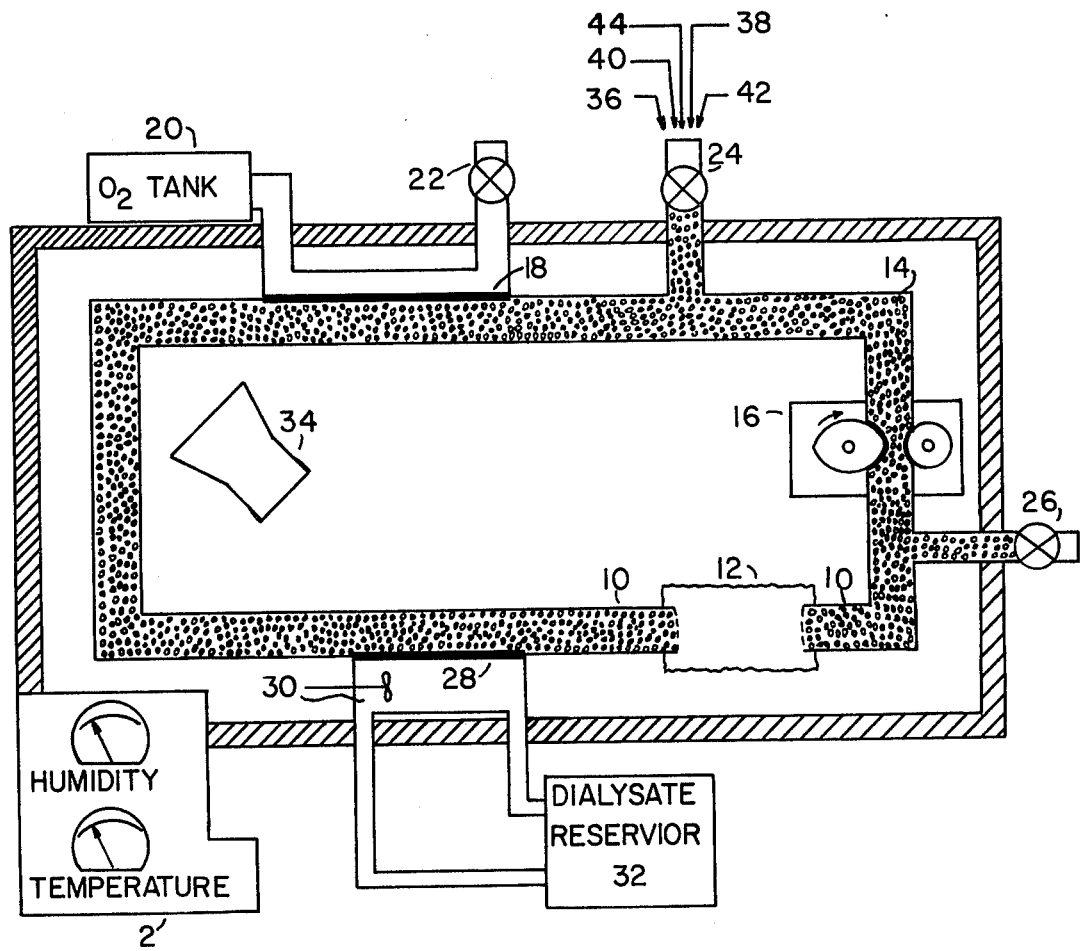
FIG. 1 is a schematic diagram showing the major components of the tissue growth support system, utilizing a growth tissue with an arterial input and venous output.
Figure 2:
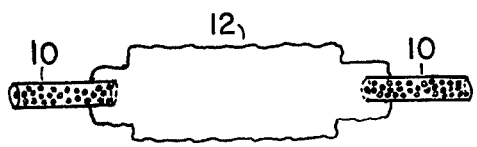
FIG. 2 is a schematic diagram showing interconnection of the tube to vascularized tissue.
Figure 3:
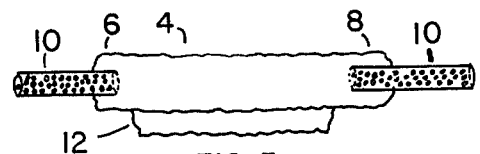
FIG. 3 is a schematic diagram showing interconnection of the tube to a mesentary supporting a growth tissue.

Referring to FIG. 1, a temperature controlled, humidity controlled antiseptic chamber 2 with appropriate gas and fluid input and output lines houses the major system components. A base tissue 4, which may be a mesentary or other tissue containing an arterial input 6 and a venous output 8, is connected to a tube 10 forming a continuous closed fluid transport system. The growth tissue 12 is normally grafted onto the base tissue 4, as in FIG. 2, but may be directly connected to tube 10 if the growth tissue 12 already has developed an arterial and venous supply system, as in FIG. 3. The tube 10 contains a solution 14 capable of transporting oxygen and nutrient to the tissue 4 and the tissue 12 and transporting carbon dioxide and waste products away from the base tissue 4 and the growth tissue 12. A pump 16 unidirectionally propels the solution 14. The tube 10 is connected to a gaseous exchange membrane 18, in turn connected to a constant regulated oxygen supply 20 and to a waste gas output vent 22. The tube 10 is connected to a supply input port 24 and a waste output port 26. The tube 10 is connected to an exchange membrane 28 allowing diffusion of waste products into a specially mixed and circulated dialysate 30, from dialysate reservior 32. Dialysate 30 may also contain nutrients ans ions necessary for tissue growth for reverse diffusion through exchange membrane 28 into solution 14. Dialysate 30 and exchange membrane 28 additionally allow water and acidity balance within the system.

In operation, the entire system is made sterile through radiation produced by an ultraviolet lamp 34 or through infused antibiotics 36. Under antiseptic conditions, growth tissue 12 is grafted onto base tissue 4 or connected directly to tube 10. Immunosuppressive drugs 38 may be added to the fluid 14 to inhibit graft vs host reactions and host vs graft reactions. Angiogenic drugs 40 and tissue growth factor 42 may be added to the system to encourage tissue growth and the formation of vasculature. Nutrients 44 are continuously infused into the system through the input supply port 24. Nutrients may also be supplied through diffusion from the circulated dialysate 30. All environmental factors, including temperature, humidity, solution acidity, oxygen consumption, nutrient supply rate, and waste removal rate are adjusted to provide a homeostatic environment most conducive to tissue growth.

The transport solution 14 may be composed of blood, with the normal white cell and platelet count reduced.

Other advantages of the present invention will be readily apparent to those skilled in the art.

I claim:

1. A method of growing tissue allowing vasular ingrowth whereby living tissue is grafted onto a non-immunoreactive mesentary, said mesentary having an arterial and venous system, said arterial and venous system is anastomosed to a tube completing a closed fluid circuit, said tube containing a solution allowing oxygen and carbon dioxide transport of a sufficient quantity for continued growth of said mesentary and said tissue, said tube is connected to a pump to unidirectionally propel said solution, said tube is connected to an artificial lung consisting substantially of a gaseous exchange membrane and a circulated supply of oxygen, said tube is connected to an artificial kidney consisting substantially of an exhange membrane and a circulated supply of dialysate, said tube is connected to an output port and an input port, and whereby a complete system comprising said mesentary, said tissue, said tube, said solution, said pump, said artificial lung, said artificial kidney, said output port, and said input port is contained in a temperature controlled, humidity controlled antiseptic housing.

2. The method of claim 1 whereby said complete system is rendered aseptic after assembly.

3. The method of claim 1 whereby tissue growth factor and angiogenesis factor are infused into said solution to encourage growth of tissue and new blood vessels.

4. The method of claim 1 whereby immunosuppressive drugs are infused into said solution to inhibit reaction of the grafted tissue to the mesentary.

5. A method of growing vascularized tissue whereby the arterial input and the venous output of a vascularized living tissue are respectively anastomosed to the ends of a tube completing a closed fluid circuit, said tube containing a solution allowing oxygen and carbon dioxide transport of a sufficient quantity for continued growth of said tissue, said tube being connected to a pump to propel said solution, said tube being connected to a gaseous exchange membrane and a circulated supply of oxygen, said tube being connected to an exchange membrane and a circulated supply of dialysate, said tube being connected to an output port and an input port, and whereby a complete system comprising said tissue, said tube, said pump, said gaseous exchange membrane, said circulated oxygen supply, said exchange membrane, said circulated dialysate, said input port and said output port is contained in a temperature controlled, humidity controlled antiseptic housing.

6. The method of claim 5 whereby said complete system is rendered aseptic after assembly.

7. The method of claim 5 whereby tissue growth factor and angiogenesis factor are infused into said input port to encourage growth of tissue and new blood vessels.

* * * * *